(12) United States Patent
Lai et al.

(10) Patent No.: US 7,132,407 B2
(45) Date of Patent: Nov. 7, 2006

(54) DNA VACCINE CONTAINING TUMOR-ASSOCIATED GENE AND CYTOKINE GENE AND METHOD OF PREPARATION THE SAME

(75) Inventors: Ming-Derg Lai, Tainan (TW); Chi-Chen Lin, Tainan (TW)

(73) Assignee: National Cheng Kung University, Tainan (TW)

( * ) Notice: Subject to any disclaimer, the term of this patent is extended or adjusted under 35 U.S.C. 154(b) by 213 days.

(21) Appl. No.: 10/663,048

(22) Filed: Sep. 16, 2003

(65) Prior Publication Data

US 2005/0020520 A1 Jan. 27, 2005

(30) Foreign Application Priority Data

Sep. 24, 2002 (TW) ............................... 91121934 A

(51) Int. Cl.
| | |
|---|---|
| *C12N 15/26* | (2006.01) |
| *C12N 15/12* | (2006.01) |
| *A61K 31/711* | (2006.01) |
| *C12N 15/861* | (2006.01) |
| *C12N 15/867* | (2006.01) |

(52) U.S. Cl. ....................... 514/44; 536/23.1; 536/23.4

(58) Field of Classification Search ..................... None
See application file for complete search history.

(56) References Cited

U.S. PATENT DOCUMENTS

| 5,998,174 A | * | 12/1999 | Glorioso et al. | ........... 435/91.4 |
| 6,797,506 B1 | * | 9/2004 | Cotten et al. | ............ 435/235.1 |
| 2002/0193329 A1 | * | 12/2002 | Hand-Zimmermann et al. | . 514/44 |

OTHER PUBLICATIONS

Pasquini et al., Gene Therapy, Apr. 2002, vol. 9, pp. 503-510.*
Lin et al., Mol. Therapy, 2004, vol. 10, No. 2, pp. 290-301.*

* cited by examiner

*Primary Examiner*—David Guzo
(74) *Attorney, Agent, or Firm*—Bacon & Thomas, PLLC

(57) ABSTRACT

The present invention discloses a DNA vaccine and the method of preparation preparing the same, which employs DNA recombination technique to co-incorporate a fragment of tumor-associated gene and a fragment of cytokine gene into a vector. The administration of such DNA vaccine can enhance the immune response of the host through the co-expression of tumor-associated protein and cytokine, and thereby achieve the therapeutic effect of inhibiting or retarding tumor growth.

5 Claims, 3 Drawing Sheets

Primer Sequence Used in Constructing N'-neu-IL-2 Fusion DNA Vaccine

|  | Primer | Sequence |
|---|---|---|
| SEQ ID NO:1 | Hind III- N'-neu(F) | 5' GCAATCGC*AAGCTT*CCGCAATGATCATCATGGAGCT 3' |
| SEQ ID NO:2 | N'-neu-Not I(R) | 5' GCAATCA*GCGGCCGC*GCTCTGCTGGGCAGCCTCGTT 3' |
| SEQ ID NO:3 | I-IL2(F) | 5' GCAATCA*GCGGCCGCC*AGCGCACCCACTTCAAGCTC 3' |
| SEQ ID NO:4 | xba I(R) | 5' GCAATCGC*TCTAGA*GGAGGTACATAGTTATTGAGGG 3' |

FIG. 1

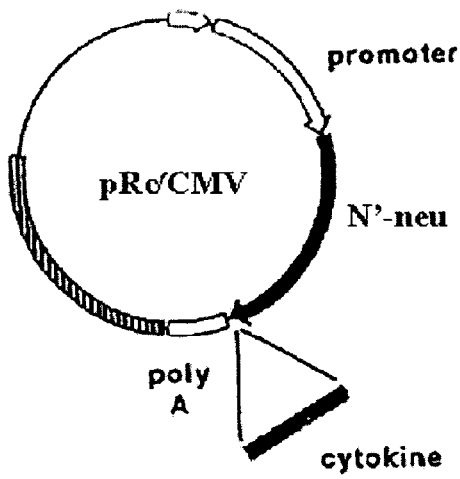

Diagram of Plasmid Containing N'-neu-IL-2 Fusion Gene

FIG. 2

DNA VACCINE CONTAINING TUMOR-ASSOCIATED GENE AND CYTOKINE GENE AND METHOD OF PREPARATION THE SAME

BACKGROUND OF THE INVENTION

1. Field of the Invention

The present invention relates to a DNA vaccine and its preparation, which employs DNA recombination technique to co-incorporate at least one fragment of tumor-associated gene and at least one fragment of cytokine gene into a vector, thereby producing a DNA vaccine containing at least one fragment of tumor-associated gene and at least one fragment of cytokine gene simultaneously.

2. Description of Related Art

The immunotherapy for cancer is drawing more and more attention in recent years. In particular, due to the development of molecular biology and the progress of biotechnology, there has been a significant breakthrough in DNA vaccine development. Current available cancer vaccines include at least DNA vaccine, dendritic cell vaccine and gene-modified tumor vaccine etc. Unlike a typical vaccine used for disease prevention, cancer vaccine aims at cancer treatment. More specifically, the purpose of cancer vaccine is to boost self-immunity for tumor cells and enable the immune system to recognize as well as kill tumor cells. DNA vaccine transforms genes encoding specific tumor-associated antigens (e.g. oncogene such as neu, met or ras) into host cells where said tumor-associated antigens are expressed through transcription and translation to induce the immune response of the host against said tumor-associated antigens and to inhibit or suppress the growth of tumor cells.

Take oncogene neu (also known as Her-2 or c-erbB-2) as an example, previous studies indicated that neu gene was over-expressed in the tumor tissues of some patients with lung cancer, breast cancer, ovarian cancer or bladder cancer. Oncogene neu encodes a transmembrane glycoprotein, which is a growth factor receptor receiving signals to expedite cell growth and division. Since the overexpression of neu gene and propagation of tumor cells are positively related, neu gene may be considered as a tumor-associated antigen. In addition, the overexpression of neu gene is also related to drug resistance in medication; patients with such symptom usually have poor prognosis.

Because of its overexpression in certain types of cancer, neu gene can be used to design cancer vaccines targeting the gene itself, for instance, a DNA vaccine carrying neu gene. The combination of neu DNA vaccine and cytokine-specific tumor vaccine, such as Interleukin-2 (IL-2), Interleukin-4 (IL-4), and GM-CSF (granulocyte macrophage colony-stimulating factor) has shown its capability to inhibit the growth of tumor cells in mice. However, the preparation of such tumor vaccine requires prolonged in vitro culture and an extra tumor cells screening process. While culturing, mutation is prone to occur and results in the loss of surface antigen; while screening, the heterogeneity of the tumor cells might decrease and reduce the protection of tumor vaccine. Moreover, it is costly to prepare this type of vaccine, and its clinical application is still not popular so far.

SUMMARY OF THE INVENTION

In order to address the drawbacks of prior arts, the present invention provides an easily prepared and relatively low-cost DNA vaccine and the method of preparing the same. Aforesaid DNA vaccine is prepared by implanting at least one fragment of tumor-associated gene and at least one fragment of cytokine gene into a vector that contains one or more suitable promoters and/or one or more translation regulating sequence. The resulted DNA vaccine contains one or more tumor-associated genes and one or more cytokine genes.

The expression of tumor-associated genes and cytokine genes implanted into the aforesaid vector may be regulated by one or more mammalian promoters and/or the IRES (internal ribosome entry site).

Another purpose of the present invention is to provide a method to construct a DNA vaccine containing at least one fragment of tumor-associated gene and at least one fragment of cytokine gene, comprising: designing primers with specific restriction sites; amplifying said tumor-associated gene fragments and cytokine gene fragments by polymerase chain reaction (PCR) and isolating the two fragments respectively; ligating the tumor-associated genes and cytokine genes with a vector containing one or more promoters and/or one or more translation regulating sequences by ligase.

The aforesaid tumor-associated genes and cytokine genes on the vector may be arranged in such an order that the tumor-associated genes are located in front of or in back of the cytokine genes.

The aforesaid construction method comprises at least: combining the tumor-associated genes and the cytokine genes as a fusion gene controlled by one promoter; or having two independent genes controlled respectively by two separate promoters; or having two independent genes regulated by a promoter and an IRES respectively.

The aforesaid DNA vaccine may be transformed at least by retroviral vector, adenoviral vector, adeno-associated viral vector, or liposome, or administered directly in the form of DNA.

The aforesaid DNA vaccine may be administered at least by subcutaneous injection, intramuscular injection, oral administration, spraying or gene gun injection.

BRIEF DESCRIPTION OF THE DRAWINGS

FIG. 1 shows the primer sequences designed for Embodiment 1 in the present invention.

FIG. 2 shows the N neu-IL-2 fusion DNA vaccine in Embodiment 1 in the present invention.

DETAILED DESCRIPTION OF THE INVENTION

Figure 3:
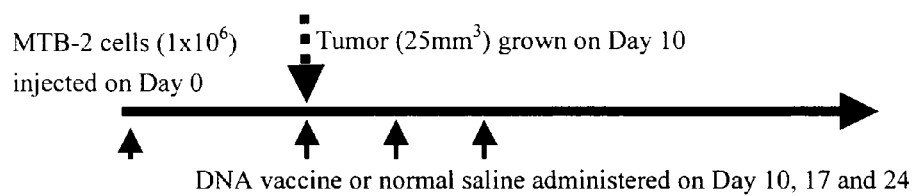
FIG. 3 is the flow chart of Embodiments 2, 3 and 4 in the present invention.

The present invention relates to a DNA vaccine and its preparation, which employs DNA recombination technique to co-implant at least a fragment of tumor-associated gene and at least a fragment of cytokine gene into a vector. The administration of an effective dose of such DNA vaccine in mammalian may enhance the immune response of the hosts through the co-expression of tumor-associated genes and cytokine genes, and thereby achieve the therapeutic effect of inhibiting or suppressing tumor growth.

The main purpose of the present invention is to provide a DNA vaccine, which is prepared by implanting at least one fragment of tumor-associated gene and at least one fragment of cytokine gene into a vector containing one or more suitable promoters and/or one or more translation regulatory sequences. The resulted DNA vaccine contains both tumor-associated genes and cytokine genes.

The expression of tumor-associated genes and cytokine genes implanted into the aforesaid vector may controlled at least by one or more mammalian promoters, such as CMV promoter, PSV promoter or LTR promoter, or regulated by IRES. Aforesaid tumor-associated genes may be full length or truncated oncogenes, such as neu, met or ras, for example, a fragment of N neu gene encoding the extracellular domain of neu protein. Aforesaid cytokines gene include at least IL-2, IL-4 or GM-CSF gene.

Another purpose of the present invention is to provide a method to construct a DNA vaccine containing at least one fragment of tumor-associated gene and at least one fragment of cytokine gene, comprising: designing primers containing specific restriction sites; amplifying said tumor-associated gene fragments and cytokine gene fragments by polymerase chain reaction (PCR) and isolating the two fragments respectively; ligating the tumor-associated genes and cytokine genes with a vector containing one or more promoters and/or one or more translation regulating sequence by ligase.

Aforesaid tumor-associated genes may be located in front of or in back of the cytokine genes on the vector. The aforesaid construction can be achieved at least by combining the tumor-associated genes and the cytokine genes into a fusion gene controlled by one promoter, for instance, fusing N neu gene and IL-2 gene behind a CMV promoter; or having two independent genes controlled by two separate promoters respectively, for instance, inserting N neu gene and IL-2 gene respectively behind two separate promoters; or having two independent genes that are respectively controlled by a promoter and an IRES segment, for instance, inserting N neu gene behind CMV promoter and IL-2 gene behind IRES.

The aforesaid DNA vaccine is transformed by retroviral vector, adenoviral vector, adeno-associated viral vector, or liposome, or administered directly in the form of DNA. The aforesaid viral vectors offer higher transfection efficiency and better expression, but each of them has its limitation. For instance, retroviral vector can only transfect cells in division; adenoviral vector leads to induce strong immune response; and adeno-associated viral vector has limited gene capacity. Non-viral vectors described above, such as liposome is very safe, but its transfection efficiency and expression are not as desirable as viral vectors. The proper vector for DNA vaccine of the present invention can be selected based on the practical needs. On the other way, the DNA vaccine can put into practice by directly injecting DNA into muscle cells, and muscle cells will automatically uptake the DNA and express it, which is sufficient to elicit enhanced immune response despite of the relatively low expression level.

The DNA vaccine herein may be administered at least by way of subcutaneous injection, intramuscular injection, oral administration, spraying or gene gun injection.

BRIEF DESCRIPTION OF THE PREFERRED EMBODIMENTS

The preparation and efficacy of DNA vaccine in the present invention are further depicted with the illustration of embodiments.

Embodiment 1

Making a DNA Vaccine by Fusing N neu Gene and Mature IL-2 Fragment

In this embodiment, DNA recombination technique is used to make a DNA vaccine containing N neu gene encoding the extracellular domain of neu protein and a mature IL-2 fragment. The preferred primer sequences for constructing the DNA vaccine of present invention, as used herein, includes the forward Hind -N'-neu primer (SEQ ID NO: 1), the reverse N'-neu-Not primer (SEQ ID NO:2), the forward Not -IL2 primer (SEQ ID NO:3) and the reverse IL-2-xba primer (SEQ ID NO:4). FIG. 1 shows the preferred primer sequence for constructing a DNA vaccine containing the fusion of N'-neu gene and mature IL-2 fragment in the present invention. The steps include designing a proper restriction site and isolating the desired N neu gene and full length IL-2 fragment using polymerase chain reaction, and after restriction enzyme digestion, adding ligase to first constructing N neu gene on a mammalian expression vector pRC/CMV, and then using restriction enzyme and ligase to insert a full length IL-2 fragment downstream of N neu gene to form a DNA plasmid containing N neu-IL-2 fusion gene. As shown in FIG. 2, the DNA plasmid is transformed into *Escherichia coli* DH5α for mass reproduction and then extracted with Endofree Oiagen plasmid-Mega kits to complete the preparation of a DNA vaccine containing the fusion of N neu gene and mature IL-2 fragment.

Embodiment 2

The Tumor-Suppressing Effect of N neu-IL-2 Fusion DNA Vaccine

Figure 4:
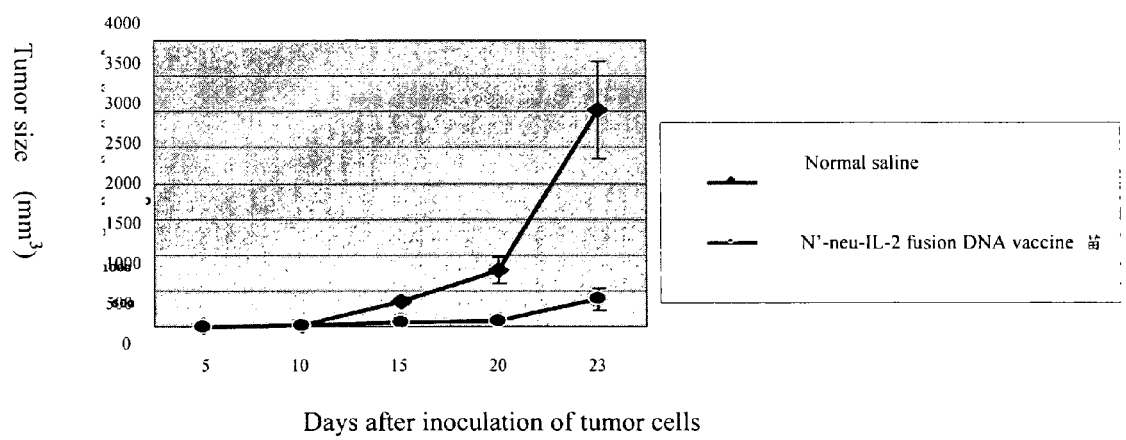
FIG. 4 shows the tumor-suppressing effect of N neu-IL-2 fusion DNA vaccine depicted in Embodiment 2 in the present invention.

In this embodiment, mice were injected with 1*10$^6$/ml MBT-2 bladder cancer cells on the back to induce tumor growth. Ten days later, N neu-IL-2 fusion DNA vaccine prepared according to Embodiment 1 or normal saline (as control) was administered intramuscularly in the first time into the tumor site. The second and third administrations of vaccine took place on day 7 and day 14 after the first administration respectively (see FIG. 3 referring to the flow chart). The sizes of tumors measured at the first administration and 2–3 times each week afterwards are shown in FIG. 4. It is found that in comparison with normal saline, N neu-IL-2 DNA vaccine has remarkable tumor-suppressing effect.

Embodiment 3

The Effect of N neu-IL-2 Fusion DNA Vaccine on the Survival Rate of Mice

Figure 5:
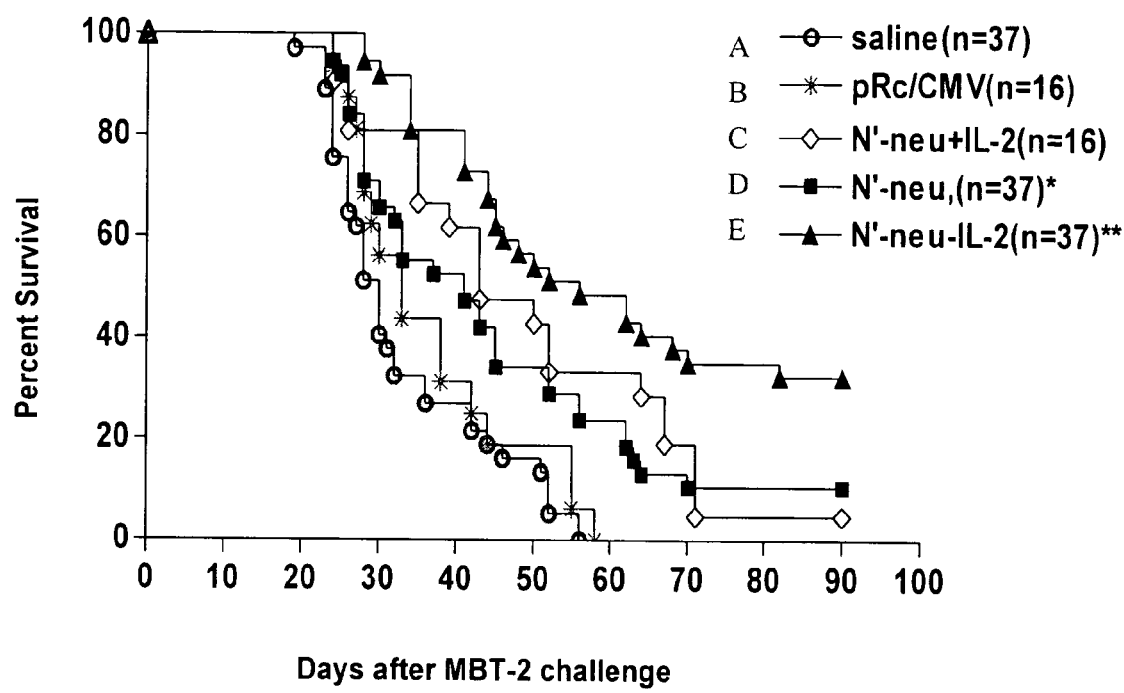
FIG. 5 shows the survival rates of mice injected with saline (5 a), pRc/CMV vector only (5 b), separate N neu DNA vaccine and IL-2 DNA vaccine (5 c), N neu DNA vaccine (5 d) or N neu-IL-2 fusion DNA vaccine (5 e) in Embodiments 3 and 4 in the present invention.

In this embodiment, mice were injected with 1*10$^6$/ml MBT-2 cells on the back to induce tumor growth. Ten days later, tumor approximately 25 mm$^3$ in size grew from the injection site, and N neu-IL-2 fusion DNA vaccine prepared according to Embodiment 1 was administered intramuscularly in the first time into the tumor; some mice received normal saline or DNA vaccine containing only N neu, but not IL-2 as control groups. The second and third administrations of vaccine took place on day 7 and day 14 after the first administration respectively (see FIG. 3 for flow process). As shown in FIG. 5, all mice (37) administered with normal saline died in 56 days after being inoculated with MBT-2 cells (line a), while 8 of the 37 mice that received N neu DNA vaccine survived (survival rate of 22% as shown in line d), and 18 of the 37 mice that received N neu-IL-2 fusion DNA vaccine survived (survival rate of 49% as shown in line e). If the observation time was extended another three weeks, that is, 90 days after the inoculation of MBT-2 cells, only 4 out of 37 mice that were administered with N neu DNA vaccine survived (survival rate of 11%, as shown in line d), while 12 out of 37 mice that received N neu-IL-2 survived (survival rate of 32% as shown in line e). The results suggest that N neu-IL-2 fusion DNA vaccine is more effective than N neu DNA vaccine in slowing down the growth of tumor, and more effectively prolonging the life of mice in the long run.

Embodiment 4

Comparing the Effect of N neu-IL-2 Fusion DNA Vaccine and the Combination of N neu Vaccine and IL-2 Vaccine Given Separately on the Survival Rate of Mice To further demonstrate the progressive nature of the prevent invention, this embodiment compares the effect of N neu-IL-2 fusion DNA vaccine and the combination of N neu vaccine and IL-2 vaccine given separately on tumor suppression. The method of tumor cell injection and the time for administering DNA vaccines in this experiment are shown in FIG. 3. The results, as illustrated in line c and line e, show that 90 days after the mice were injected with MBT-2 cells, 12 out of 37 mice administered with N neu-IL-2 fusion DNA vaccine survived (survival rate of 32% as shown in line e), while only 1 out of 16 mice administered with combination of N neu vaccine and IL-2 vaccine given separately lived (survival rate of 6% as shown in line c), further indicating the superior effect of N neu-IL-2 fusion DNA vaccine.

The DNA vaccine of the present invention has been disclosed in the embodiments. However the embodiments should not be construed as a limitation on the spirit and scope of the appended claims. Those skilled in the art can easily understand that all kinds of alterations and changes can be made within the spirit and scope of the appended claims.

The DNA vaccine of the present invention containing tumor-associated gene and cytokine gene offers several advantages: (1) It can induce cellular and humoral immune responses which last for a long time; (2) the expressed antigen has a structure that approximates that expressed in human body during natural infection, thereby producing better immunization effect; (3) it can cross recognize different parts of the antigen, which helps overcome the problem of vaccine escape mutant; (4) combined immunization may be carried out by inserting combination of different antigen genes in the plasmid; (5) it has a variety of administration routes, including subcutaneous, intramuscular, oral, spray or gene gun; and (6) its preparation process is simple and cost-effective. It is also easy to mass produce, transport and preserve. It is an improvement over known cancer-treating vaccines and demonstrates better efficacy.

What is claimed is:

1. A DNA vaccine containing N'-neu-IL-2 fusion gene controlled by a CMV promoter.

2. The DNA vaccine according to claim 1, wherein the N'-neu portion of said fusion gene comprises a truncated segment of neu gene encoding extracellular domain of neu protein.

3. The DNA vaccine according to claim 1, wherein the N'-neu portion of said fusion gene is upstream or downstream of the (IL)-2 portion of said fusion gene.

4. The DNA vaccine according to claim 1, wherein said DNA vaccine is carried by retroviral vector, adenoviral vector, adeno-associated viral vector, or liposome, or said DNA vaccine is administered directly in the form of DNA.

5. The DNA vaccine according to claim 1, wherein it is administered by way of subcutaneous injection, intramuscular injection, oral administration, spraying or gene gun injection.

* * * * *

SEQUENCE LISTING

```
<160> NUMBER OF SEQ ID NOS: 4

<210> SEQ ID NO 1
<211> LENGTH: 36
<212> TYPE: DNA
<213> ORGANISM: Artificial
<220> FEATURE:
<223> OTHER INFORMATION: primer

<400> SEQUENCE: 1
gcaatcgcaa gcttccgcaa tgatcatcat ggagct                36

<210> SEQ ID NO 2
<211> LENGTH: 36
<212> TYPE: DNA
<213> ORGANISM: artificial
<220> FEATURE:
<223> OTHER INFORMATION: primer

<400> SEQUENCE: 2
gcaatcagcg gccgcgctct gctgggcagc ctcgtt                36

<210> SEQ ID NO 3
<211> LENGTH: 36
<212> TYPE: DNA
<213> ORGANISM: artificial
<220> FEATURE:
<223> OTHER INFORMATION: primer

<400> SEQUENCE: 3
```

```
gcaatcagcg gccgccagcg cacccacttc aagctc                              36
```

<210> SEQ ID NO 4
<211> LENGTH: 36
<212> TYPE: DNA
<213> ORGANISM: artificial
<220> FEATURE:
<223> OTHER INFORMATION: primer

<400> SEQUENCE: 4

```
gcaatcgctc tagaggaggt acatagttat tgaggg                              36
```